United States Patent [19]

Weber et al.

[11] 4,082,004

[45] Apr. 4, 1978

[54] CROSSCUT SAMPLER

[75] Inventors: Joseph A. Weber, Arlington, Tex.; Hugo Wenshau, Burnsville, Minn.

[73] Assignee: Gustafson, Inc., Hopkins, Minn.

[21] Appl. No.: 787,370

[22] Filed: Apr. 14, 1977

[51] Int. Cl.² .............................................. G01N 1/20
[52] U.S. Cl. ................................ 73/422 R; 73/423 R
[58] Field of Search .......................... 73/422 R, 423 R

[56] References Cited

U.S. PATENT DOCUMENTS

| 2,759,362 | 8/1956 | Pate | 73/423 R |
|---|---|---|---|
| 3,253,470 | 5/1966 | Platzer et al. | 73/423 R |
| 3,298,235 | 1/1967 | Platzer | 73/423 |
| 3,747,411 | 7/1973 | McDermott et al. | 73/423 R |

Primary Examiner—S. Clement Swisher

Attorney, Agent, or Firm—H. Dale Palmatier

[57] ABSTRACT

A crosscut sampler attachable into the conveying pipes of a pneumatic or gravity system and including an elongate sample collecting head having a slot-like entrance port and facing the entrance opening of the housing, the head being elongate and tapering divergently from said entrance port and being mounted on a slidable mounting tube slidably extending through the sidewall of the housing; there being a closure to lie flush against the front face of the housing and tightly seal the slot-like entrance when the head is in rest position, an air cylinder for moving the head and mounting tube transversely of the flow passage in the housing and a collecting container for the samples of granular or particulate material.

14 Claims, 6 Drawing Figures

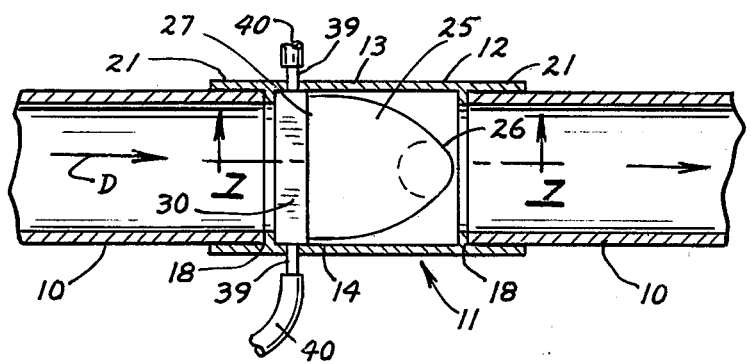
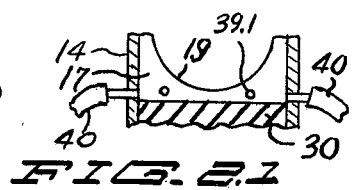
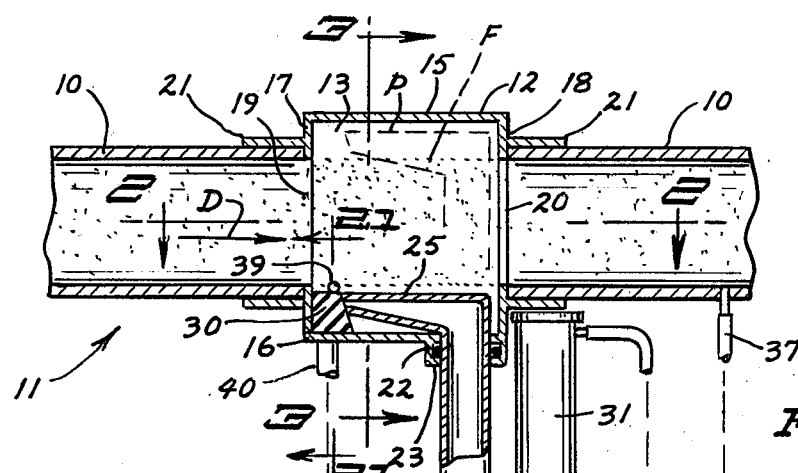
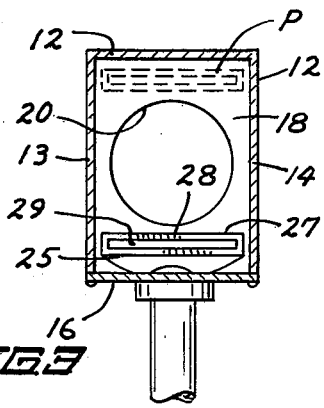
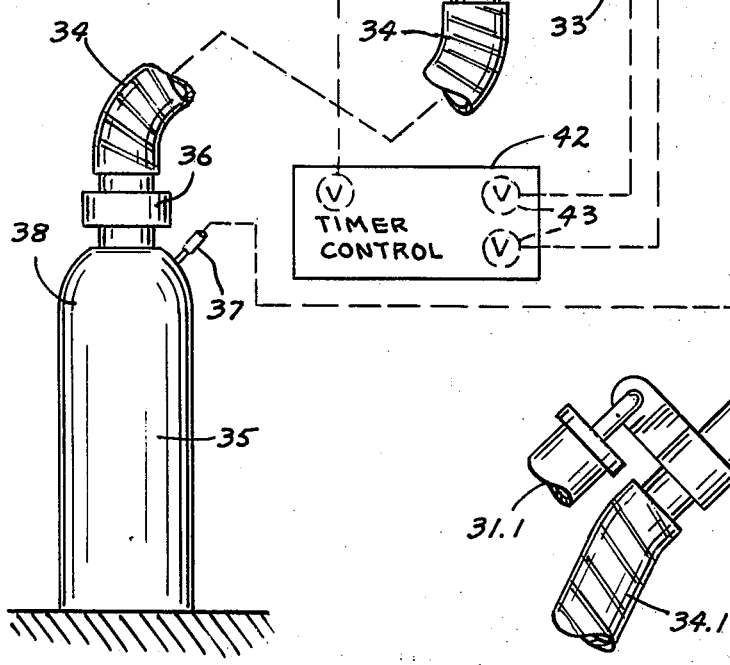
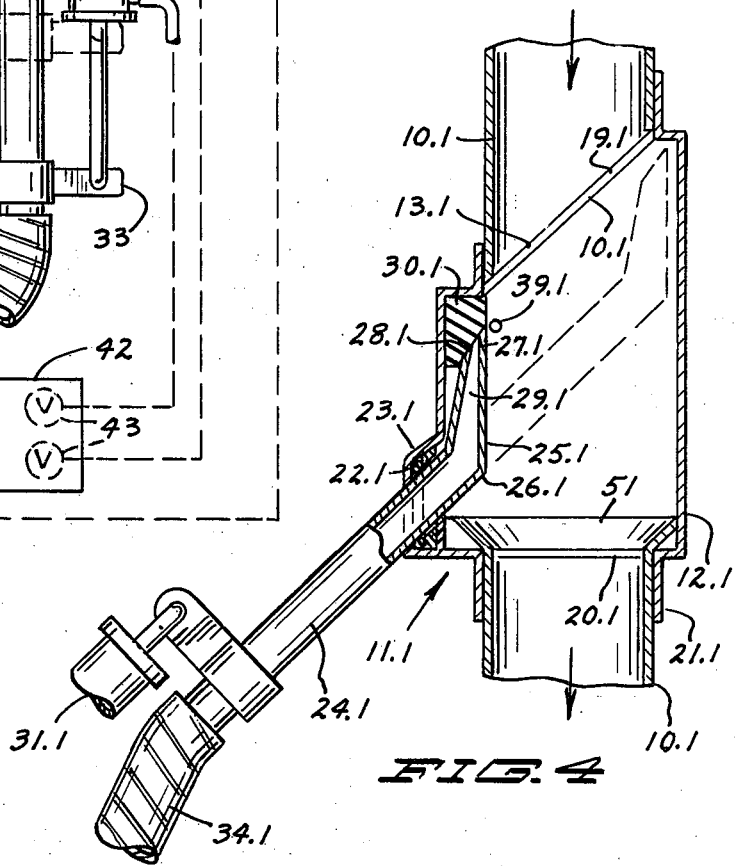

CROSSCUT SAMPLER

This invention relates to apparatus for obtaining a crosscut sample of granular or particulate material flowing in a conveying tube which has an air pressure which is significantly different than ambient air pressure.

BACKGROUND OF THE INVENTION

The importance of periodic sampling of granular or particulate materials flowing in a conveying tube under the influence of air for moving the material in the tube or under the influence of gravity, has become to be recognized as being very important in the day-to-day operation of many different types of manufacturing facilities and in the handling of various types of material as for processing.

Crosscut samplers for acquiring samples of granular or particulate material flowing in conveying tubes have, in the past, been particularly awkward and outsized, and have not been particularly efficient for the purpose intended. The sample collecting heads have not previously had the capability to be efficiently and simply sealed so that separate and distinct samples can be taken so that there is no interference or crossover as between the samples which are taken.

SUMMARY OF THE INVENTION

The present invention embraces an apparatus for collecting and withdrawing samples of granular or particulate material which is flowing in a conveying tube and which may be propelled by air moving through the tube. The sampler is well adapted for use with vacuum systems as well as pressurized air conveying systems.

A housing is inserted into the conveying tube, and the housing has an open interior between flow openings in the end walls of the housing so as to define an unobstructed flow passage through the housing. Access into the housing by the sampler need only be at one location, and the sampling head is moved across the flow passage in the housing so as to collect a sample of the flowing material. The sample collecting head has an elongate and thin shape oriented along the passage for the flowing material so as to minimize interference with the natural flow of material through the head and flow passage. The head is mounted by a tube which also carries away the collected samples, and the mounting tube for the head is disposed well away from the front face of the collecting head so that the tube will not interfere with the natural flow of material through the passage and so that the slot shaped entrance into the sampling head will collect a truly representative crosscut of the material flowing.

The end face of the sampling head through which the entrance slot opens, seals at the lower side of the housing each time the sampling head returns to its rest position so that the material collected in the sampling head will be restricted to only that material which is moving through the flow passage at the time the sampling head is intentionally being moved across the flow of material.

In order to provide for the efficient sealing of the entrance to the sampling head at the end of each cycle of operation, the head is retracted out of the flow passage for the flowing material, and the end face is seated against a closure element carried in the housing so that the slot in the end face of the sampling head is very tightly closed. As a result, no dust or other particles of the material flowing in the system will collect at or inadvertently find its way into the sampling head between the intermittent cycles of operation.

In one desirable form, the mounting tube is slidably mounted in a bearing at one side of the enclosed housing so as to slidably move into and out of the housing and across the flow passage of moving material. The head is carried on the tube in a similar direction. The closure at the side of the housing and the end face of the head are both similarly oriented and at an acute angle with respect to the sliding direction of movement of the tube and head as they traverse the flow passage so that the end face of the sampling head, when retracted from the flow passage, will bear firmly against the closure in sealing relation.

The housing in the conveying tube also has at least one and in many instances two air blast nozzles directed at the closure to facilitate directing a jet of air at the closure in the last instant before the head is seated against the closure, whereby to clear away any granular or particulate material that may have collected on the closure which would otherwise prevent an efficient seal from being made as the head comes to its resting place against the closure between cycles of operation.

The head mounting tube which slides into and out of the housing is connected by a flexible hose to a sample collecting bottle which may be mounted nearby.

BRIEF DESCRIPTION OF THE DRAWINGS

FIG. 1 is a longitudinal section view through a portion of the conveying tube and the sampler, substantially as indicated at 1.1 of FIG. 2.

FIG. 2 is a detail section view taken approximately at 2—2 in FIG. 1.

FIG. 2.1 is a detail section view taken at 2.1—2.1 of FIG. 1.

FIG. 3 is a transverse section view taken approximately at 3—3 of FIG. 1.

FIG. 3.1 is a detail elevation view of a modified sampling head.

FIG. 4 is a longitudinal section view of a modified form of the invention.

DETAILED SPECIFICATION

The preferred form of the invention is illustrated in FIGS. 1 - 3 of the drawings. Conveying tubes 10 are a part of a pneumatic conveying system for conveying granular or particulate material, of which flour is one example. The pneumatic conveying system causes air to sweep through the tubes or pipes 10 and carry the granular or particulate material with it. In some instances, the pneumatic conveying system will maintain a vacuum pressure or subatmospheric pressure in the pipes 10, and in other instances, depending upon the type of installation, a superatmospheric pressure may be found in the pipes of the conveying system.

The sampling apparatus is indicated in general by numeral 11, and includes a rigid rectangular housing 12 having sidewalls 13 and 14, top and bottom walls 15 and 16, and end walls 17 and 18. The several walls of the housing are integral with each other and in one piece excepting the bottom wall which is secured to the side and end walls by screws and is sealed to the remainder of the housing by a suitable air sealing gasket.

The end walls 17 and 18 have flow openings 19 and 20 therein, and if the direction of movement of the granular or particulate material, which is indicated by the arrow D, is taken into consideration, the flow opening 19 may be considered an entrance port and the opening 20 may be considered an exit or discharge port. It will be recognized that the openings 19 and 20 are aligned with each other and have substantially the same interior size as is the interior size of the conveying pipes 10 to which the housing 12 is connected. The housing, together with the openings in the end walls thereof, define an unobstructed flow passage F through the interior of the housing which, at the front face 28 of head 25, has approximately the same width or diameter as the diameter of the opening 19 and of the interior diameter of the pipe 10. The flow passage is depicted in FIG. 1 by the stippling which denotes the existence of concentrations of the particulate or granular material flowing through the central portion of the housing interior.

End walls 17 and 18 have rigid fittings or bosses 21 affixed thereon for securing the ends of the conveying pipes 10 to the housing. Of course, if necessary, suitable clamps, mechanical fasteners, and air pressure sealing materials may be used to hold the housing and pipes together and to obtain an efficient air seal.

The bottom wall 16 has a bearing opening 22 formed therein and suitable packing 23 to create an air seal around the periphery of the bearing opening. A rigid metal mounting tube 24 extends through the bearing opening 22 and is slidable therein.

The sample collecting head 25 is mounted on the upper end of rigid tube 24 such that the rear end of the interior of the sample collecting head communicates with the interior of the tube 24. It will be noted that the head 25 flares from the rear end 26 to the front end 27 thereof so that the entrance end 27, which is immediately adjacent the entrance port 19, extends entirely across the width of the flow passage in the interior of the housing and entirely across the diameter of the entrance port 19.

The head 25 has a thin and longitudinally tapering profile as seen in FIG. 1 so that the thickness of the head is significantly less than the diameter of the entrance opening 19 and of the flow passage for the granular or particulate materials moving through the housing.

The front face 28 of the head has an elongate slot-like entrance 29 formed therein and it will also be noted that, particularly in FIG. 3, the entrance slot 29 extends across the full width of the openings of the housing end walls.

In sampling certain powder-like materials such as flour, it may be desirable to use a modified form of head 25a, see FIG. 3.1, having a plurality of small apertures 29a through the front face 28a and extending into the open interior of the head, instead of the single entrance slot 29. The number and size of the holes 29a may be varied, according to the nature of material being sampled, and the size of the sample sought, but the holes will be regularly spaced along the full length of the elongate front face 28.

The mounting tube 24 will be reciprocated longitudinally of its length so as to move the sample collecting head 25 entirely across the width of the interior of the housing and entirely across the flow passage of materials moving through the housing. The sample collecting head 25 is illustrated in FIG. 1 in its normal rest position, which it normally assumes between operating cycles, and the alternate position of the head is indicated by the letter P in dotted lines in FIGS. 1 and 3.

The front face 28 of the sample collecting head 25 lies substantially in a plane which is tipped at an oblique angle with respect to the direction of linear movement of the head 25 and tube 24, as illustrated in FIG. 1.

The housing 12 has a stationary closure 30 mounted adjacent the lower wall 16 and affixed in the housing to be immovable. The closure 30 is preferably constructed of stiff but slightly yieldable hard rubber or plastic and has a sealing face which has the same oblique orientation as the front face 28 of the sample collecting head. Accordingly, when the sample collecting head 25 is retracted into its rest position as illustrated in FIG. 1, the closure 30 confronts and bears tightly against the front face 28 of the head which has been moved against the closure so as to tightly seal the slot entrance 29 against accidental entrance of other granular material or dust in between sampling cycles.

An air cylinder 31 having an extendible piston rod 32 is secured by a bracket 33 to the mounting tube 24 for the purpose of reciprocating the tube 24 and head 25 through the desired operating cycle. The lower end of the mounting tube 24 is connected to a flexible hose 34 for conveying the samples of materials into a closed sample container 35. The container 35 is provided with a detachable fitting 36 so that the samples collected can be easily dumped for analysis.

The container 35 is provided with a small pressure equalizing hose or tube 37 which is connected by suitable fittings to the conveying pipe 10 to allow for flow of air which is necessary in order to admit samples of the material into the collecting head 25. The hose 37 is utilized when the pressure in the pipes 10 is subatmospheric; and when a superatmospheric pressure is used in the pipes 10, the hose 37 may be eliminated, and the fittings capped, and a pet cock 38 will be opened to relieve air pressure in the container. The pet cock 38 is provided with a suitable filter to prevent escape of collected samples.

A pair of air nozzles or tubes 39 extend through opposite sidewalls of the housing immediately adjacent the closure 30 to direct jets of air along the closure and in the vicinity of the front face 28 of the head as the head is being seated upon the closure.

Additional nozzles or air openings 39.1 are provided in the end wall 17 to direct jets of air directly into the entrance of the head instantaneously before the head seats and is closed, for the purpose of clearing the head of any granular or particulate material that might be lodged therein. The jets of air thus produced will unseat any collected granules of material and allow an efficient seal relation to be established between the head and the closure 30. Of course, the arrangement of the nozzles 39 and 39.1 may be varied slightly, depending mostly upon the exact surface contours of the housing interiors. For instance, the nozzles 39 might be closer to the front wall 17 if certain materials lodge in the corners; and additional nozzles 39.1 may be provided as needed at the front wall 17. The front wall may be considerably thicker to accommodate a manifold opening through which air is supplied to nozzles 39.1. Air is supplied to the nozzles or fittings 39 through hoses 40, the air to which is controlled by a valve 41 in a timed control or mechanically controlled apparatus indicated in general by numeral 42. Suitable valves 43 are provided for controlling the air applied to the cylinder 31, and these valves 43 are also operated by the timed control. Preferably, the valve 41 is opened while the cylinder 31 is being retracted so as to clear the adjacent side space of the housing and the closure as the head is approaching to be seated.

In the form of the invention illustrated in FIG. 4, the conveying pipe or tube 10.1 is shown to be oriented vertically. In this instance, the air pressure within the pipe 10.1 is substantially the same as atmospheric pressure, and there is no significant pressure differential between the pressure within the pipe and atmospheric pressure. The pipe simply allows the granular or particulate material therein to flow by gravity rather than under the influence of rapidly moving air. It should, however, be understood that the use of a vertical pipe is not limited to gravity systems, but may also be used in a pneumatic conveying system. However, the present conveying pipe 10.1 is intended to illustrate the gravity flow system.

The sampling apparatus 11 includes a flat sided housing 12.1 with substantially flat and planar sidewalls and annular collars 21.1 on the ends of the housing to receive and mount the ends of the pipes 10.1. Suitable O-ring gaskets or other sealing devices may be used to produce an efficient seal between the collars and the conveying pipes. The end walls of the housing have flow openings or ports 19.1 and 20.1 to receive the stream of flowing granular or particulate material flowing in the pipes 10.1. It will be noted that the end wall at opening 19.1 is obliquely oriented with respect to the longitudinal orientation of the pipe 10.1, and the end face 10.11 of the upper pipe section is also obliquely cut so as to extend as close as possible to the sample collecting head 25.1.

The housing is provided with a contoured guide panel 51 adjacent the port 20.1 for guiding all of the particulate material out of the housing and downwardly into the pipe section 10.1 as to prevent any collection of the particulate material in the housing. Preferably, the panel 51 is tapered convergently from the sidewalls of the housing and into a generally conical shape immediately adjacent the opening 20.1 which is circular in configuration.

The sample collecting head 25.1 is shaped almost identically to the head 25 illustrated in FIGS. 1 – 3 and is similarly mounted on a rigid tube 24.1, but in the arrangement of FIG. 4, the tube 24.1 is oriented somewhat differently with respect to the head 25.1 than the tube to head arrangement in FIG. 1. It will be noted that the tube 24.1 is obliquely oriented in a downwardly and outwardly extending direction and as illustrated, the tube 24.1 extends at an angle of approximately 45 degrees to the vertical so that granular and particulate material falling into the sampling head 25.1 will continue to travel by gravity downwardly through the tube 24.1 and through the flexible hose 34.1 to a collecting container which may be substantially similar to that illustrated in FIG. 1.

The head 25.1 has a broad and rather flat front end 27.1 substantially identical in shape to the front end portion of the head 25 in FIG. 1. Similarly, the head 25.1 has a substantially flat and planar front face 28.1 which is oriented to obliquely face the entrance port 19.1 of the housing when the head 25.1 is extended out into the flow stream. The front face 28.1 of the head is oriented at an oblique and acute angular relationship to the direction of movement of the head 25.1, which direction of movement is controlled by the orientation of tube 24.1. Accordingly, when the head 25.1 is retracted into the rest position illustrated in full lines in FIG. 4, the front face 28.1 will seat firmly against a closure 30.1 which is affixed in the side space of the housing. One face of the closure 30.1 is oriented identically to the orientation of the front face 28.1 of the head so that when the head is retracted into the rest position, the sealing face of the closure 30.1 and the front face 28.1 of the head lie flush against each other.

Head 25.1 also has a slot-like entrance 29.1 so as to extend, in its longitudinal direction, entirely across the width of the central passage in the housing through which the granular or particulate material flows which is of essentially the same size as the diameter of the entrance and exit ports 19.1 and 20.1. When the head 25 is moved across the flow passage, the head will assume the dotted line position D wherein the slot 29.1 is again entirely out of the flow passage so that representative samples from all portions of the cross-sectional area of the flow of material will be collected. It will be recognized in this form of the invention that the tube 24.1 is connected to the rear portion 26.1 of the head so that when the head is extended into the stream of flowing material, there is essentially no disruption of the stream of flowing material by the tube 24.1, insofar as there might be any effect upon the collecting of a sample at the entrance slot 29.1.

The housing is provided with a suitable slide bearing 23.1 and a suitable seal 22.1 at the opening in the sidewall through which the tube 24.1 extends.

Reciprocation of the head and tube is effected by an air cylinder 31.1 in a manner similar to that described in connection with FIGS. 1 – 3.

The sidewalls 13.1 of the housing are provided in this form of the invention with air nozzles or inlets 39.1 immediately adjacent the closure 30.1 and the front end portion 27.1 of the head for the purpose of directing a jet of air across the closure 30.1 immediately prior to the instant when the head 25.1 seats against the closure so as to assure that the front face 28.1 of the head seats firmly in face to face relation on the closure.

It will be seen that we have provided a new and improved crosscut sampler particularly adapted for pneumatic conveying systems wherein the elongate head of thin profile has an entrance slot which sweeps across the entire stream of flowing granular or particulate material in the sampling housing. The entrance is disposed well away from the mounting tube which carries the head across the housing and back to its rest position. When the head is returned to its rest position between cycles of operation, the slot-like entrance is entirely sealed shut so as to prevent entrance into the collecting head of any of the material flowing through the housing or any dust that might wander into the unobstructed side portion. The head also lies substantially flush with the side face of the closure so that no unusual obstructions or crevices remain in which unwanted quantities of dust or materials might collect. As a result, materials will enter the head only when the head is intentionally extended out into the stream of flowing materials, and until the head reaches the extreme dotted line position illustrated wherein the head is in the open and unobstructed side portion of the housing, and thereafter when the head is immediately returned to the rest position so that the entrance slot is sealed shut.

During the interval when the head is located in the stream of flowing material, the granular or particulate material will fall into the head by gravity and will fall further by gravity through the mounting tube and then through the flexible hose into the container to be stored temporarily. In the use of the sampling apparatus with a pneumatic system, the granular or particulate material is actually swept into the head by flowing air and the material then falls through the tube and into the container. The air which sweeps the material into the head then escapes from the container, either through the hose or through the partially open pet cock.

What is claimed is:

1. Apparatus for drawing a representative sample of granular or particulate material flowing in a conveying pipe of a pneumatic conveying system, comprising a sealed housing with aligned entrance and exit flow openings for connection into the conveying pipe, the housing having an open interior with an unobstructed central passage aligned with the flow openings to permit free flow of the material-laden air moving through the pipe, the housing also having open interior side spaces adjacent the central passage, means collecting samples of the material flowing through the central passage of the housing and including a sample collecting head in the housing and movable therein to and between said side spaces and in a first direction transversely of the central passage and entirely through said central passage, the head having a front face oriented to confront the entrance opening of the housing and also oriented at an oblique angle with respect to said first direction, the head also having an elongate entrance in said front face to permit access of such flowing material into the sample collecting head, said entrance extending entirely across the central passage in a direction transversely of said first direction, an elongate mounting slide carrying said collecting head and also extending transversely outwardly through one side of the housing and being slidably mounted thereon, and a closure mounted in one of said side spaces of the housing and having a sealing surface to abut and seal against the front face of the sample collecting head to entirely close the entrance to the head when the head is moved out of the flow passage, the sealing surface of said closure also being oriented obliquely of said first direction and lying along and in the direction of said front face to lie flush against the front face of the head.

2. The apparatus according to claim 1 and the slide comprising a rigid tube connected to and communicating with the interior of the head, a closed storage container, and means connecting the storage container to the tube to receive samples of material therefrom.

3. The apparatus according to claim 1 and including an air nozzle on the housing and directed toward the side space of the housing interior adjacent the closure.

4. A crosscut sampler for granular and particulate materials which are flowing rapidly in a closed conveying pipe, comprising a closed housing having opposite end walls with aligned flow openings therein to communicate with such a conveying pipe and means for attachment to the conveying pipe, the housing having an open interior defining an unobstructed flow passage between the flow openings in the end walls, the housing also having a side wall with a bearing opening therein, an elongate sample collecting head in the housing and extending toward said end walls and longitudinally along the flow passage, the head having an entrance end adjacent one of the flow openings and a rear end adjacent the bearing opening, the entrance end having an elongate slot therethrough to admit entrance of such materials into the head, the slot extending entirely across the flow passage and having a length approximating the width of the adjacent flow opening, the entrance end of the head having a width, in a direction transversely of the slot, which is substantially less than the width of the adjacent flow opening of the housing, the head also having a tapered shape in its longitudinal direction and progressively tapering divergently from the entrance end to the rear end, an elongate rigid mounting tube connected to the rear end of the sample collecting head in widely spaced relation with the entrance end thereof, the mounting tube extending outwardly through the bearing opening of the sidewall of the housing and being slidable inwardly and outwardly through said bearing opening and transversely of the elongate flow passage in the housing to progressively carry the sample collecting head transversely across the flow passage in both transverse directions, the width of the mounting tube being significantly less than the width of the sample collecting head and also substantially less than the length of the entrance slot, means connected to said mounting tube for reciprocating the tube longitudinally thereof, and container means having flow connection with said mounting tube to receive and store the samples of material collected by the head.

5. The crosscut sampler according to claim 4 wherein said entrance end of the head has a front face which is obliquely oriented at an acute angle with respect to the direction of sliding movement of the mounting tube, and a stationary closure in the head at one side thereof and in confronting relation with the front face of said entrance head to engage and close the entrance slot when said head is moved transversely across the passage and then into engagement with the closure.

6. The crosscut sampler according to claim 5 and an air nozzle extending through the sidewall of the housing and directed along the closure to apply a jet of cleaning air to remove the granules and dust from the closure immediately prior to engagement of the entrance end of the head thereon.

7. The crosscut sampler according to claim 4 wherein the mounting tube extends transversely of the flow passage and substantially perpendicular to the elongate sample collecting head.

8. The crosscut sampler according to claim 4 and the mounting tube extending transversely of the flow passage in an oblique direction and extending at an oblique and obtuse angle with respect to the elongate sample collecting head.

9. The crosscut sampler according to claim 8 and said housing having an end wall and entrance port extending obliquely with respect to said flow passage and lying substantially parallel with the oblique orientation of said mounting tube.

10. The crosscut sampler according to claim 4 and said mounting tube extending in a downward direction from the head.

11. Apparatus for drawing a representative sample of granular or particulate material flowing in a conveying pipe of a pneumatic conveying system, comprising a sealed housing with aligned entrance and exit flow openings for connection into the conveying pipe, the housing having an open interior with an unobstructed central passage aligned with the flow openings to permit free flow of material-laden air moving through the pipe, the housing also having open interior side spaces adjacent the central passage, means collecting samples of the material flowing through the central passage of the housing and including a sample collecting head in the housing and movable therein to and between said side spaces and in a first direction transversely of the central passage and entirely through said central passage, the head having an elongate front face oriented to confront the entrance opening of the housing and also oriented at an oblique angle with respect to said first direction, the head also having entrance means in said front face to permit access of such flowing material into the sample collecting head, said entrance means providing access into the head at at least several locations along the length of said elongate front face, an elongate mounting slide carrying said collecting head and also extending transversely outwardly through one side of the housing and being slidably mounted thereon, and a closure mounted in one of said side spaces of the housing and having a sealing surface to abut and seal against the oblique front face of the sample collecting head to entirely enclose the entrance means when the head is moved out of the flow passage, the sealing surface of said closure also being oriented obliquely of said first direction and lying along and in the direction of said front face to lie flush against the front face of the head.

12. The apparatus according to claim 11 and said entrance means comprising an elongate slot-like opening extending substantially throughout the length of said elongate front face of the head.

13. The apparatus according to claim 11 and said entrance means comprising a plurality of discrete apertures spaced along the length of said elongate front face.

14. The apparatus according to claim 13 and said front face having a length of the same order of magnitude as the width across the entrance flow opening of the housing, and said elongate front face having a width which is significantly less than the width across the entrance flow opening of the housing.

* * * * *